United States Patent [19]

Carter et al.

[11] Patent Number: 5,126,034
[45] Date of Patent: Jun. 30, 1992

[54] BIOELECTROCHEMICAL ELECTRODES

[75] Inventors: Nigel F. Carter, Oxon; Christopher J. Hammond, Cambs; Monika J. Green, Bucks; Paul I. Hilditch, Oxon; Stephen C. Williams, Oxon, all of Great Britain

[73] Assignee: Medisense, Inc., Cambridge, Mass.

[21] Appl. No.: 383,202

[22] Filed: Jul. 21, 1989

[51] Int. Cl.[5] .......................................... G01N 27/26
[52] U.S. Cl. .................................. 204/403; 204/412; 204/431
[58] Field of Search ............... 204/197, 412, 403, 400, 204/415, 431

[56] References Cited

U.S. PATENT DOCUMENTS

| | | | |
|---|---|---|---|
| 2,884,366 | 3/1958 | Anderson et al. | 204/400 |
| 3,235,477 | 2/1966 | Keyser et al. | 204/415 |
| 3,509,034 | 4/1970 | Paine | 204/412 |
| 3,969,209 | 7/1976 | Mueller | 204/412 |
| 4,500,391 | 2/1985 | Schmidt et al. | 204/431 |
| 4,521,290 | 6/1985 | Venkatasetty | 204/412 |
| 4,534,356 | 8/1985 | Papadakis | 204/431 |
| 4,614,716 | 9/1986 | Rohrback et al. | 204/403 |
| 4,655,880 | 4/1987 | Liu | 204/403 |
| 4,735,691 | 4/1988 | Green et al. | 204/431 |
| 4,863,578 | 9/1989 | Webster | 204/197 |
| 4,871,440 | 10/1989 | Nagata et al. | 204/412 |
| 4,897,173 | 1/1990 | Nankai et al. | 204/412 |
| 4,929,426 | 5/1990 | Bodai et al. | 204/400 |
| 4,963,245 | 10/1990 | Weetall | 204/412 |
| 5,000,180 | 3/1991 | Kuypers et al. | 204/412 |

Primary Examiner—John Niebling
Assistant Examiner—Bruce F. Bell
Attorney, Agent, or Firm—Fish & Richardson

[57] ABSTRACT

A disposable element is provided for use in analytical equipment for electrochemical determination of biological cells. The disposable element comprises a working electrode, a reference electrode, and a filter for retention of solids in the vicinity of the electrodes. The analytical equipment with disposable elements can be used for respiratory assays, enzyme assays or immunoassays, among other uses.

In a variation, the disposable element comprises a reference electrode, working electrode and fusible link.

13 Claims, 5 Drawing Sheets

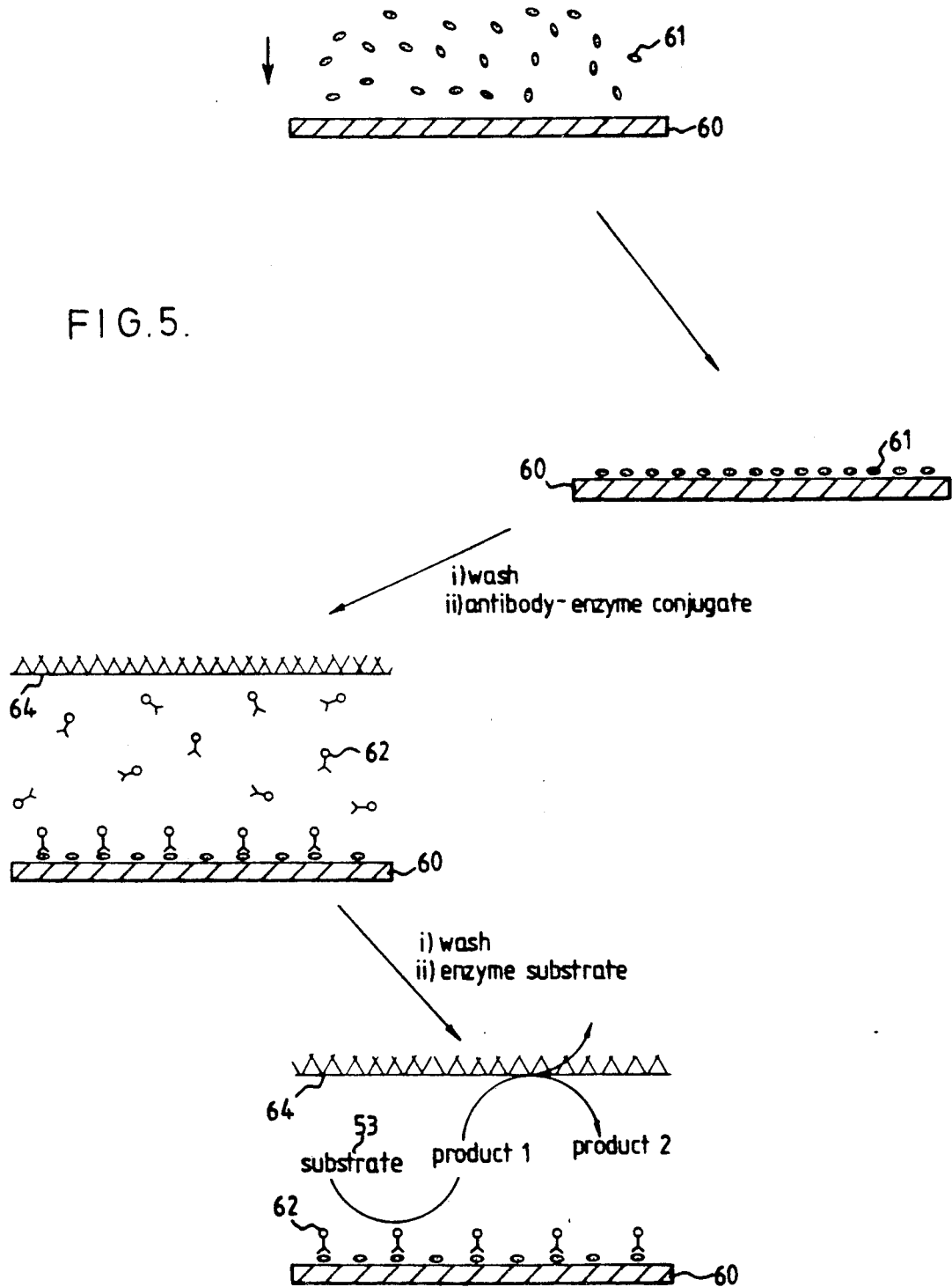

BIOELECTROCHEMICAL ELECTRODES

BACKGROUND OF THE INVENTION

The present invention relates to analytical equipment for performing electrochemical assays on microbial samples. In particular, the present invention relates to electrodes for use in such analytical equipment.

Accurate and rapid determination of microbial activity is essential in many areas, including pollution control; quality assurance in the food, drink and drugs industries; and clinical analysis of bodily fluids and other medical samples.

For a long time, the standard method for the enumeration of bacteria has been an agar plate count. This method has many disadvantages, especially the time needed to obtain results. Even with the fastest growth, 18 hours is needed for visible colony formation, and then there is the task of counting the colonies.

There have been proposals to employ bioelectrochemical cells or fuel cells for assaying or microbiological samples. For example, amperometric determination of viable cell numbers based on sensing microbial respiration is described in Appl Microbiol Biotechnol (1981) 12. 97; the use of a microbial fuel cell for the rapid enumeration of bacteria is described in Appl Microbiol Biotechnol (1988) 28, 26; and an investigation of a simple amperometric electrode system to rapidly quantify and detect bacteria is described in J Appl Bacteriol (1989) 66, 49. Further aspects of amperometric bioassay systems are described in EP 190470 and 238322, and GB 2181451 and 2181558, among other examples. Some of these systems employ a filter to capture microbial cells at the electrodes, after which the determination is effected.

OBJECT OF THE INVENTION

The aim of the present invention is to permit development of analytical equipment for electrochemical determination of microorganisms and other cells which can be repeatedly used to give reliable results.

SUMMARY OF THE INVENTION

The present invention provides analytical equipment for a bioelectrochemical determination of microorganisms or other cells in a liquid sample using a working electrode and a reference electrode. The working electrode, the reference electrode, and a filter for retention of solids in the vicinity of the electrodes are provided as a disposable element. The analytical equipment has receiving means for releasably receiving the disposable element.

Since the electrodes and filter are provided as a disposable element, the user of the analytical equipment does not have to set up the electrodes and arrange the filter. A greater degree of certainty and reliablity is introduced by employing the disposable element, which may be carefully manufactured as a sealed unit under controlled conditions to a consistent quality.

The disposable elements themselves are part of this invention, and in further aspects, the present invention provides methods of assay for microorganisms or other cells which methods employ the disposable elements.

PREFERRED EMBODIMENTS OF THE INVENTION

The disposable element in conjunction with the associated analytical equipment is suitably designed for through-flow use to trap any cells in the sample, effecting concentration and allowing washing. At present a generally planar disposable element is preferred, especially for use with the electrodes and filter extending generally horizontally, and with flow through the element being generally vertical.

The filter of the disposable element maybe interposed between opposed electrodes, or in alternative constructions, the filter can be upstream of the electrodes. The choice of filter material depends on three main criteria: good retention of biological cells (90% or better); adequate flow rate at a given pressure; and reasonable resistance to blockage. The last two criteria affect the volume of a particular sample that can be introduced and hence the degree of concentration obtainable.

Particularly suitable filters are depth filters, especially glass fibre filters (for example, as manufactured by Whatman or Millipore). Other filters can be employed, such as membrane filters, charge-modified filters, and so on. Alternative forms of filters might be adopted, including capture matrices such as antibodies or lectins immobilised on beads. The filter may be housed in a housing made from two halves fitted together. These two halves can be made in an injection moulding process. Furthermore, meshes can be employed to encourage the desired flow and distribution of liquid through the filter.

The working electrode may be based on known materials. It is possible to use noble metals such as gold or platinum, but it is generally preferred to use less expensive materials for the manufacture of disposable devices. A suitable material may be graphite felt (for example, RVG2000 Le Carbone). However, graphite felt tends to provide high electrical resistance, and in a preferred aspect of this invention, it has been found that good results are available from the use of printed carbon electrodes. In a particularly preferred aspect, one or more of the electrodes is screen printed.

The reference electrode typically comprises silver and silver chloride (Ag/AgCl), or mercury and mercury chloride (saturated calomel electrode, SCE). Such systems have known, absolute electrode potentials in aqueous media. It is preferred to use the reference electrode alone to complete the external circuit, particularly when currents are small ($10^{-6}$A or less). Especially preferred is a printed silver/silver chloride reference electrode.

Since the potential of the reference electrode can drift as current passes, it is possible to provide a counter electrode through which the bulk of the current can be directed. Suitable materials for counter electrodes include platinum, gold or silver. Where a counter electrode is used, it is sufficient that the reference electrode has enough surface area to establish the reference potential.

Screen-printed electrodes present a number of advantages: there is more scope for optimising electrode behaviour and configuration, and a close proximity of working and reference electrodes can be achieved. The resistances are lower than with graphite felt, and it is considerably easier to make contacts to the electrodes. The response of printed electrodes to bacteria are of the same order as those obtained with graphite felt, but a little lower. However, this result is compensated for by better and more controllable background currents.

The reference and/or working electrode and /or counter electrode is suitably formed by printing or otherwise coating onto an inert substrate, such as a fibre (for instance glass fibre) matrix or plastics (for instance polyvinyl chloride, "pvc") substrate. Permeability of the electrode can be an advantage, but it may be solid, provided that fluid can pass across its surface. When the electrode serves no filtering function it is equally possible to use a solid electrode with one or more apertures for passage of liquid, or to use a network or matrix allowing free passage or liquid through all parts of the electrode.

In one embodiment, the working electrode is carbon felt laid over a filter, with a matrix reference electrode positioned opposite the working electrode. The whole is placed in a housing and the sample is fed in through an entry port. This diffuses across the filter allowing the surface areas of both electrodes to be effectively used. In practice, a buffer will generally be passed through in both direction to purge any air present, before the sample is introduced, again, in either direction. This is then usefully followed by washing with buffer and introduction of compounds acting as mediators, as required.

In an alternative embodiment, the electrode through which the sample is introduced has a single aperture preferably in the centre, while an opposite electrode allows escape of fluid about its periphery, preferably through more than one aperture, for example eight apertures.

In another embodiment, a working electrode of carbon printed ink is interdigitated with a reference electrode printed in silver/silver chloride ink. For example a star-shape electrode interdigitates with the other electrode. The close proximity of reference and working electrodes allows good control of the potential at the working electrode surface. A counter electrode can be provided by a disc printed in silverr ink. The electrodes are suitably printed onto 0.5mm thick pvc, and cut into discs. Apertures punched in the discs allow liquid flow: a central aperture in the working reference electrode disc and eight peripheral apertures in the other disc being suitable. The discs can then be assembeled in a filter electrode holder on either side of a glass-fibre filter disc, to give a disposable element.

In a yet futher embodiment, the disposable element comprises a pvc or other plastics substrate with two concentric electrodes comprising a working electrode, preferably screen-printed in organic-based carbon ink, and an outer reference electrode, preferably screen-printed in silver-silver chloride ink. The concentric design is preferable to many configurations for current distribution and potential control. A three-electrode design can be envisaged, where there is a third counter electrode, either in the plane of the other two electrodes or opposite them.

In general, the electrodes may be connected to a read-out device by any suitable conducting contacts. Examples include gold, copper and platinum contacts, which may be spring-loaded or otherwise biased.

The filter electrode assembly is preferably a single-use disposable element. In order to ensure single use of the disposable element, there can be provided a fusible electrically conducting link which may be fused to ensure single use of the disposable element. For example, incorporated into an auxiliary electrode print can be a fine track of silver-silver chloride ink, spanning two contact pads. Before each assay, the equipment can verify that the disposable element is freshly installed and has not previously been used, and the fuse link is still intact. It can be arranged that the equipment will then burn out the link by applying a larger voltage.

The use of the fusible link has wiser application. For example, a range of disposable elements can be provided with different uses, each type within the range having a fusible link with a characteristic resistance. It can then be arranged that the analytical equipment can distinguish between different resistance types and make use of this information, including to optionally display or otherwise indicate the type of disposable element which has been placed in the equipment.

More generally, the fusible link can be employed in disposable elements which do not have a filter. Disposable elements comprising a working electrode and a reference electrode are described, for example, in EP 127958, and in "Biosensors Fundamentals and Applications" eds Turner, Karube and Wilson, OUP, 1987.

In accordance with a further aspect of this invention, there is provided a disposable element for use in analytical equipment for an electrochemical determination, the disposable element comprising a working electrode, a reference electrode, and a fusible electrically conducting link which may be fused to ensure single use of the disposable element.

The disposable elements lacking a filter are preferably manufactured in accordance with the disclosure in EP 127958 (published Dec. 12, 1984), which is incorporated herein by reference and to which the reader is now specifically referred. For example, the working electrode may incorporate a mediator and/or an enzyme. Such disposable elements may be designed as generally planar elements, as shown in EP 127958. Printed electrodes are preferred.

However, disposable elements without filter may have utility beyond mediated and like assays, and their general use in electrochemistry is envisaged by the present invention. The user of the analytical equipment does not have to set up the electrodes as before, and a greater degree of certainty and reliablity is introduced by employing a disposable element, which may be carefully manufactured as a sealed unit under controlled conditions to a consistent quality.

The disposable element, with or without filter, is advantageously packaged in a sealed packet, for example a packet made of plastics-coated aluminium which may be opened at the point of use.

The analytical equipment is preferably configured in conjunction with the disposable element such that there is only one way in which the disposable element can be received in the receiving means. The receiving means preferably comprises a generally horizontal recess accessed from above by a door, though other constructions are possible, including a horizontal slot accessed horizontally, a drawer, a vertical slot accessed vertically, and so on.

For preference, the engagement of the disposable element in the analytical equipment results in automatic alignment of fluid paths and electrical connections. The analytical equipment typically has its own pump, supplies of buffer, and other components. For automation of sample feeding and electrical measurement, microprocessor control is preferred. In order to ensure consistent results and maximised reponses, the analytical equipment suitably includes a heater for incubating a microorganisms retained on the filter. An air bubble sensor can be included, in order to detect air bubbles and thereby avoid false results. A suitable sensor comprises two electrodes in the fluid path.

In one method in accordance with the present invention, a respiratory assay is carried out, employing an artificial mediator compound. The precise mechanism by which respiration assays function is unclear. The process of respiration in the bacterium involves oxidative degradation of a substrate, with consequent abstraction of electrons. These electrons pass between redox agents sited in the membrane of the cell, which include proteins such as the cytochromes, and small lipophilic molecules such as quinones. In aerobic respiration, the electrons eventually participate in the reduction of oxygen. In anaerobic respiration, nitrate, fumarate, or other compounds can function as terminal oxidants. It is to be assumed that artificial mediators which are capable of becoming reduced in the presence of respiring bacteria do so by abstracting electrons from one or more of the redox agents in the membrane.

For a respiration assay, the disposable element of this invention is temporarily secured in the analytical equipment. The sample is brought in to contact with the filter, for example by flowing the sample through the disposable element, thereby capturing microorganisms on the filter. A solution of a mediator compound is then brought in to contact with the electrodes and the filter, and thus with cells captured on the filter. The working electrode is then poised at an effective potential. If the potential is such that chemical species in the solution can be reduced or oxidised at the working electrode, a current will flow through the external circuit. This current flow at the electrodes can be monitored. By comparison with results obtained under standardised conditions, a quantitative assay becomes possible.

Micro-organisms or other cells which may be assayed by the use of the present invention include Gram-positive bacteria, Gram-negative bacteria, fungi, algae, cyanobacteria, yeasts, single cell cultures, and other microbes. Specific examples of cells which may be assayed include *Pseudomonas fluorescens, Salmonella typhimurium, Listeria monocytogenes,* and *Escherichia coli.*

Mediators such as ferrocene and ferrocene derivatives may be adopted in this invention. Other mediators which may be adopted include quinones, phenazine methosulphate, and especially p-benzoquinone. The mediator is preferably supplied as a solution of effective concentration.

The use of a filter in the disposable element allows microorganisms to be concentrated from the sample, and permits washing of the sample. For example, reductants present in orange juice (such as ascorbic acid) might interfere with a respiratory assay, but such reductants may easily be flushed away, allowing measurements to be taken on the microbes alone.

The analytical equipment of the present invention may be used for enzyme assays by addition of artificial substrates releasing an electrochemically active moiety, and for immunoassays using enzyme-labelled antibodies.

For an enzyme assay, the disposable element is temporarily secured in the analytical equipment. The sample is brought in to contact with the filter. A solution of an enzyme substrate is then brought in to contact with the electrodes and the filter, the substrate being substrate for an enzyme of the organism. The enzyme is allowed to catalyse conversion of the substrate to a product having electroactivity different to that of the substrate. The working electrode is poised at an effective potential and current flow at the electrodes is detected.

Using such an enzyme assay, certain species or groups of microorganisms can be identified, characterized or quantified on the basis of enzyme activity. For example, possession of alanine aminopeptidase activity is correlated in a great many cases with Gram-staining behaviour. Such enzymes further include the aminopeptidases; specifically, pyrrolidonyl aminopeptidase (pyroglutamyl aminopeptidase), E.C. 3.4.19.3. First described from *Pseudomonas fluorescens,* the enzyme has been found to have widespread, although not universal, distribution among bacteria. The most comprehensive study (J Gen Microbiol (1970) 61, 9) of its distribution investigated some 2354 strains of the Enterobacteriaceae, and found 451 of these to display the enzyme activity.

In a preferred enzyme assay, a substrate is employed which on reaction in the presence of the enzyme releases a reporter group which is electrochemically active in free solution but not when coupled to the substrate. For example, for pyrrolidonyl aminopeptidase, a suitable substrate is N,N-dimethyl-N'-pyrrolidonylphenylene-diamine. The released moiety upon enzymatic hydrolysis is dimethylphenylenediamine, which displays an oxidation peak at $+190$mV vs SCE, the unreacted substrate oxidising only in the region of $+400$mV vs SCE. Thus, by selecting a potential of about $+250$mV vs SCE for the assay, the two substances can be distinguished.

The detection of bacteria in the respiration assay, and the determination of specific bacterial enzyme activities, allows respectively quantification of total biomass and of certain groups. A further aspect of the present invention resides in an immunoassay format.

To this end, the present invention provides a method of assaying immunologically for microorganisms in a liquid sample, based on the analytical equipment and the disposable elements comprising the working electrode, the reference electrode, and the filter. The disposable element is temporarily fixed in the analytical equipment. The sample is brought in to contact with the filter, followed by a solution of an enzyme-labelled antibody, the antibody (monoclonal or polyclonal) being one which immunoreacts with a microorganism to be determined. The labelled antibody binds to immobilised microbial antigens on microorganisms trapped at the filter. Excess unbound reagent can be removed by a wash procedure, and the enzyme label associated with the filter can be quantitated. To this end, a solution of a substrate is brought in to contact with the electrodes and the filter, being substrate for the enzyme of the enzyme-labelled antibody. The labelling enzyme is allowed to catalyse conversion of the substrate to a product of electroactivity different to that of the substrate. By poising the working electrode at an effective potential, current flow at the electrodes can be monitored. The magnitude of the current produced by oxidation (or reduction) of the product at the working electrode can be related to the microbial loading on the filter.

This method allows discrimination of different strains within the same species, or of different species or different serotypes within the same genera. For example, detection of *E. coli* is possible using a mouse anti *E. coli* monoclonal antibody and anti-mouse alkaline phosphatase conjugate, the filter being preferably blocked beforehand to reduce non-specific binding reactions. A mouse anti *E. coli* monoclonal antibody labelled with alkaline phosphatase represents another suitable reagent.

In general, for methods of this invention, it is preferred to minimise background currents, in view of the sensitivity of the assay. The true zero response is closely defined, in order to discern small signals above the response level. One method is to use an experimental protocol in which a blank measurement is made at the start of the procedure, after which sample is introduced, the reaction performed, and a second current measurement made in which the results of the reaction are assayed. The response of the instrument to the sample is then the difference between the two measurements.

The present invention will now be further illustrated with respect to the accompanying drawings, in which:

SUMMARY OF THE DRAWINGS

FIG. 5 shows stages in an immunoassay of the present invention; and

EXAMPLES OF THE INVENTION

Example 1

Disposable Element

Figure 1:
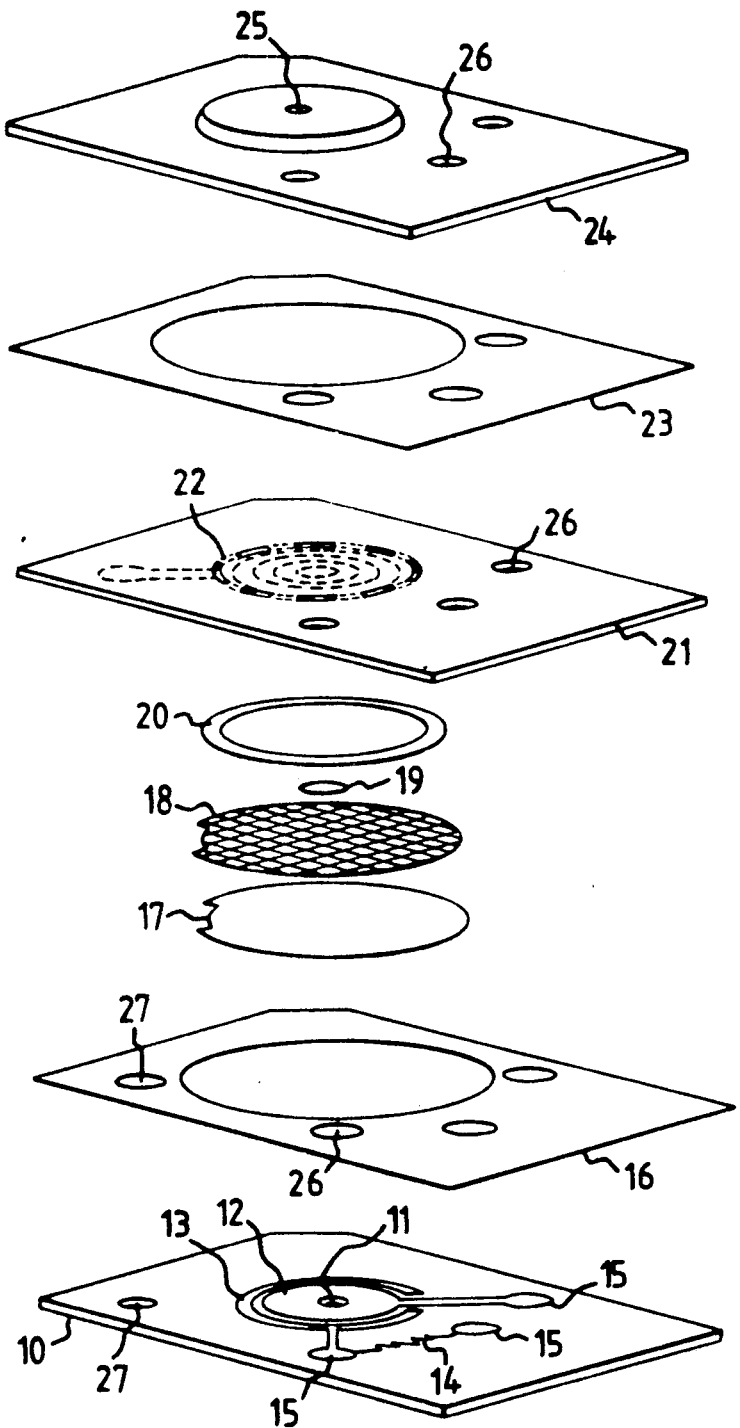
FIG. 1 shows an exploded view of a disposable element according to the present invention.

FIG. 1 is an exploded view of one embodiment of a disposable element of this invention. Considered from the bottom of the figure, the element comprises a base plate 10 with central aperture 11 and printed working electrode 12, reference electrode 13, fusible link 14 and electrical contacts 15; an adhesive layer 16; a filter membrane 17; a backing mesh 18; an impermeable centre spot 19; an adhesive ring 20; a diaphragm 21 with counter electrode 22; an adhesive layer 23; and a top cover 24 with central aperture 25. Coaxial apertures 26 extend through to the electrical contacts 15 on the base plate, and apertures 27 through to the counter electrode.

When sample is pumped through the disposable element, the diaphragm 21 flexes away from the filter 17 to allow liquid flow fully across the filter. When pumping ceases, the diaphragm relaxes and the filter is then held in close contact with the electrodes.

Example 2

Disposable Element

Figure 2A:
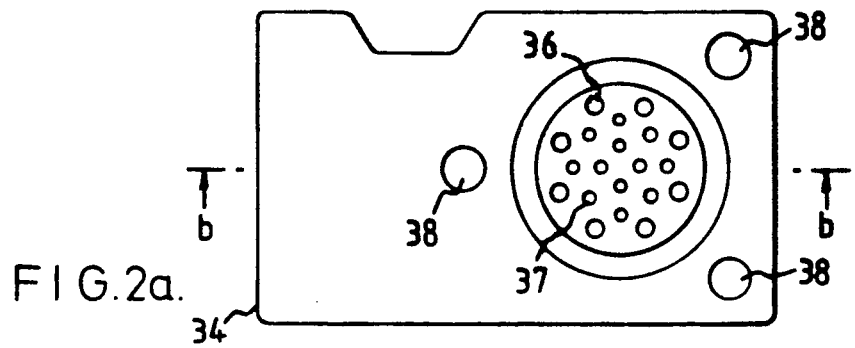
FIG. 2a, 2b and 2c respectively show a view from above, a vertical cross-section, and a printed base plate for another disposable element according to the invention.
Figure 2B:
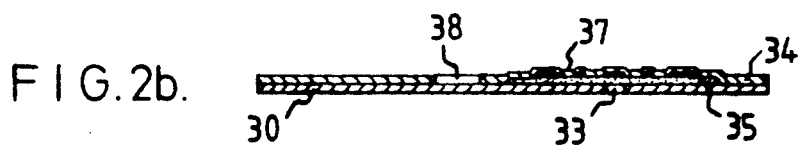
Figure 2C:
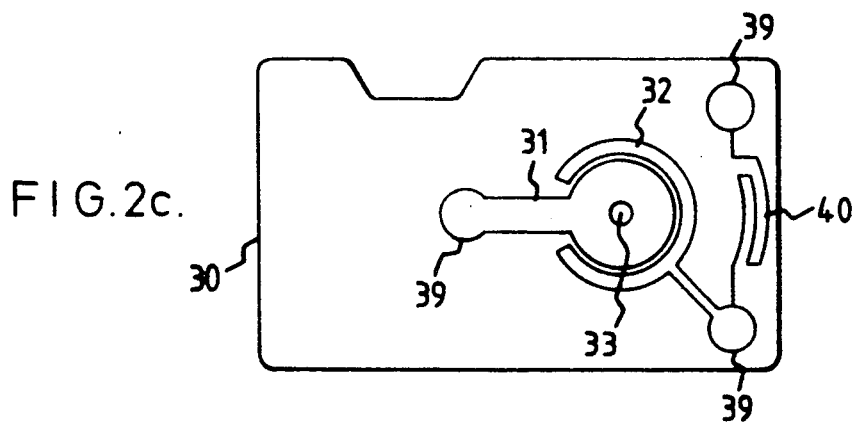

FIG. 2 illustrates the currently preferred construction for a disposable element of this invention. A base plate 30 of pvc serves as the electrode support. There are two concentric electrodes comprising a working electrode 31 screen-printed in organic-based carbon ink, and an outer reference electrode 32 screen-printed in silver/silver chloride ink, and including a fusible link 40. The base plate has one central aperture 33 for liquid ingress. An upper sheet 34 is formed to hold a filter disc 35 of glass fibre in place. A two-step recess is formed in this sheet, so that when the element is assembled, the filter disc is crushed slightly around its edge, discouraging leakage of fluid round the edge of the filter.

Outlet of fluid is through eight apertures 36 in a circle: this ensures that the whole extent of the filter within the second step of the recess is used for filtration. To further ensure the maximum possible flow rate a dimpled texture with dimples 37 is formed on the upper sheet within the eight outlet apertures. This holds the filter away from the back wall of the disposable when under pressure. Three apertures 38 in the upper sheet expose the electrode and fuse contacts 39. Although pvc is used for both halves of the disposable element, other plastics such as polycarbonate could be used. While the upper sheet of pvc is thermoformed into shape at present, this component could equally be injection-moulded in polystyrene, or made in other ways.

After assembly of the two sheets of pvc with filter disc, the two halves are adhered together with transfer adhesive, or alternatively using thin ($<5\mu m$) double-sided tape or liquid glue printed, sprayed or rollered. The disposable is then punched out into its final shape, which is essentially rectangular, with rounded corners and a notch on the left hand side ensuring correct insertion into the housing shown in FIG. 4.

Figure 3:
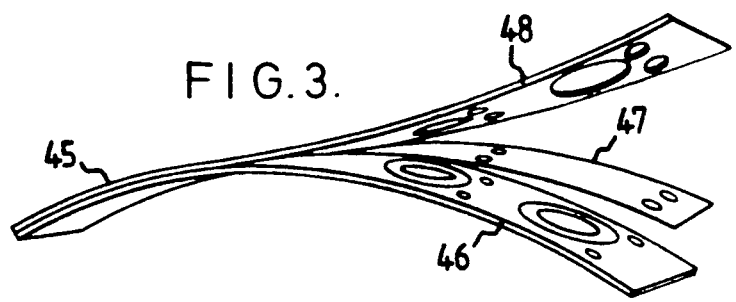
FIG. 3 shows a continuous tape providing multiple disposable elements of this invention.

In a further embodiment shown in FIG. 3 of the disposable element, the disposable elements can be provided as a continuous tape, as illustrated in the figure in partially exploded form, with a continuous bottom ribbon 46 carrying the electrodes, a continuous filter ribbon 47, and a continuous embossed upper ribbon 48. Such a tape is particulary useful with analytical equipment having an automated step-wise feed for sequentially feeding the elements in turn in to position for repeated assays.

Example 3

Analytical Equipment

Figure 4:
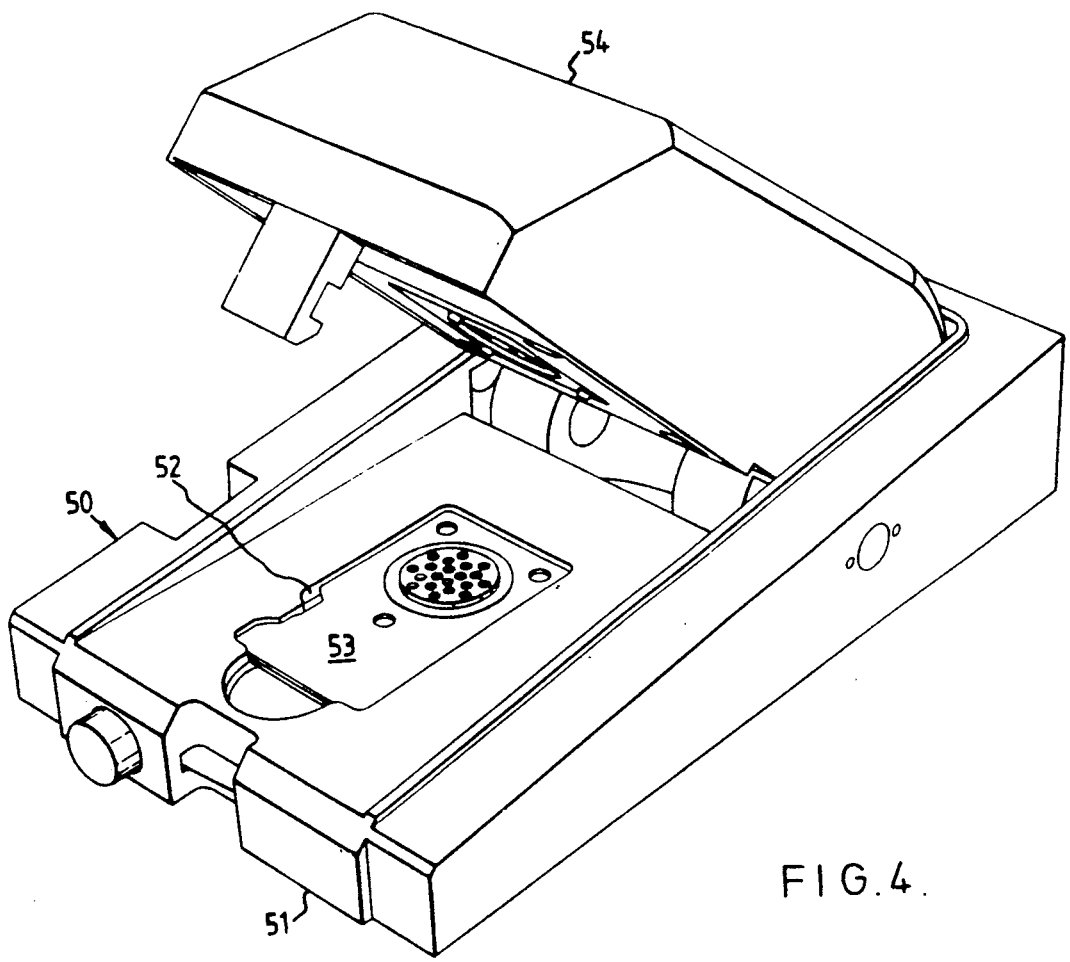
FIG. 4 shows a perspective view in open configuration of analytical equipment according to the present invention.

The views of FIG. 4 generally illustrate the analytical equipment 50 in accordance with this invention. Within a housing 51 is a generally horizontal recess 52 for receiving a disposable element 53, and means (not shown) for fluid handling, temperature control, and electronic hardware. The equipment is designed to make automatic electrical and fluid connections to the disposable element placed in the recess when the lid 54 of the housing is latched shut.

The measurement system includes a thermostatted heater, a fluid handling system with a pump, switching valves, and air-bubble sensor, a potentiostat for measuring current transients, and a single card computer, associated interfaces and micro disc drive. The unit carries out the following functions:
i) maintains the filter cell at a preset temperature
ii) pumps through the cell measured quantities of sample and reagents.
iii) applies a potential and measures the resulting integrated current response.
iv) calculates the microbial concentration.
v) inputs data from the user such as batch numbers, sample data, and outputs the result of the assay.
vi) stores the results and data and printed output.
vii) checks at all stages for errors such as end of reagent, previously used cell or fluid blockage, and provides interlocks to prevent mishandling.

The analytical equipment of FIG. 4 with disposable elements of FIG. 2 can be employed, for instance, in a respiratory assay, for which the following protocols are appropriate:

A. Simple protocol
1. Introduce sample.
2. Wash with buffer/electrolyte.
3. Introduce mediator/buffer/electrolyte.
4. Incubate for specified period at specified temperature.
5. Apply potential and measure current.

B. Protocol with lower-value calibration
1. Flush system with mediator/buffer/electrolyte. Wait for specified temperature.
2. Apply potential, measure current. Record as null value.
3. Wash with buffer/electrolyte.
4. Continue from (A1) above.

EXAMPLE 4

An Immunoassay

Referring to FIG. 5, sample is passed through the disposable element of FIG. 2, capturing bacteria 61 on the filter 60. Soluble components in the sample are removed by a wash reagent, which is followed by a solution of antibody-enzyme conjugate 62. The antibody used is designed to bind specifically with a particular genus, species (or serotype) of microorganism and is covalently coupled to an enzyme reporter group to facilitate detection. Following a simple wash step to remove excess unbound reagent, the enzyme label now intimately associated with the filter is quantified with an appropriate substrate 63. The enzyme (such as alkaline phosphate) converts substrate to an electroactive product, in known manner, whose concentration is determined by oxidation/reduction at the electrode surface 64.

The resultant current is then in direct proportion to the number of bacteria trapped in the filter. The immunoassay format thus not only allows identification of specific bacteria (by virtue of the antigen-antibody interaction), but also direct enumeration of the species concerned.

EXAMPLE 5

A respiratory assay

Following insertion of the disposable element of FIG. 2 in to the housing of FIG. 4, 10 ml of phosphate/chloride buffer (100 mM sodium phosphate, 100 mM sodium chloride, pH 6.8, containing 10 mM glucose) was pumped in an upward direction. Sample was then introduced, followed by buffer to wash medium components from the filter. The assembly was next flooded with the buffer solution, containing 1.25 mM p-benzoquinone. The whole was then incubated at 37° C., typically for 10 minutes, after which time a potential of +400 mV vs Ag/AgCl was applied to the working electrode and the current recorded.

The following table shows the responses ($\mu$A at t=30 seconds, corrected for background) obtained for four different microorganisms at various dilutions in appropriate media.

| Microrganism | cfu/ml | response |
|---|---|---|
| Bacillus cereus | $1 \times 10^7$ | 4.2 |
| (NCFB 1771) | $1 \times 10^5$ | 0.5 |
| Pseudomonas | $2 \times 10^8$ | 8.0 |
| fluorescens | $2 \times 10^3$ | 1.0 |
| (NCTC 10038) | | |
| Escherichia | $1.3 \times 10^8$ | 10.0 |
| coli | $1.3 \times 10^6$ | 1.6 |
| (NM 522) | $1.3 \times 10^4$ | 0.6 |

| Microrganism | cfu/ml | response |
|---|---|---|
| Serratia | $7.7 \times 10^8$ | 23.6 |
| marcescens | $7.7 \times 10^6$ | 4.5 |
| (ATCC 14756) | $7.7 \times 10^4$ | 1.0 |

EXAMPLE 6

Screening of Bacteria

The response of a benzoquinone respiration assay with several species of bacteria was tested, and the relative responses of the different bacteria measured. The reaction was carried out in 100 mM sodium phosphate buffer, pH 6.8, containing 100 mM sodium chloride. Glucose was included at 10 mM, and p-benzoquinone was present at 1.25 mM (p-benzoquinone was obtained from BDH, and recrystallised from 40°-60° petroleum ether). Bacteria were grown in either nutrient broth (Gibco BRL) or in yeast glucose broth (nutrient broth plus 0.3% w/v yeast extract; 0.5 % (w/v) glucose, pH 6.8) but were washed and resuspended in 100 mM sodium phosphate pH 6.8; 100 mM sodium chloride; 10 mM glucose prior to assay. Bacteria were either added directly to the cell along with mediator solution, and incubated at known temperature for a given time, or the incubation was performed remotely from the cell and the solution transferred to the cell for measurement. The currents were normalised for cell numbers (as estimated by standard plate count) and expressed relative to the response of E. coli NM522 taken as 100. The results are presented in the following table.

TABLE

| | Response |
|---|---|
| Bacillus badius ATCC 14574 | 50 |
| Bacillus cereus NCFB 1771 | 3098 |
| Bacillus sphaericus ATCC 14577 | 375 |
| Bacillus subtilis NCFB 1769 | 2159 |
| Escherichia coli NM 522 | (100) |
| Pseudomonas fluorescens ATCC 25289 | 4.5 |
| Salmonella typhimurium ATCC 13311 | 50 |

Data for Bacillus cereus and Bacillus subtilis are included in the table, but the plate-count results for these organisms were surprisingly low (hence the large normalised responses). There is scatter within the data, but the assay detected all the species of bacteria tested and there was no correlation with species or Gram-staining behaviour.

EXAMPLE 7

Figure 6A:
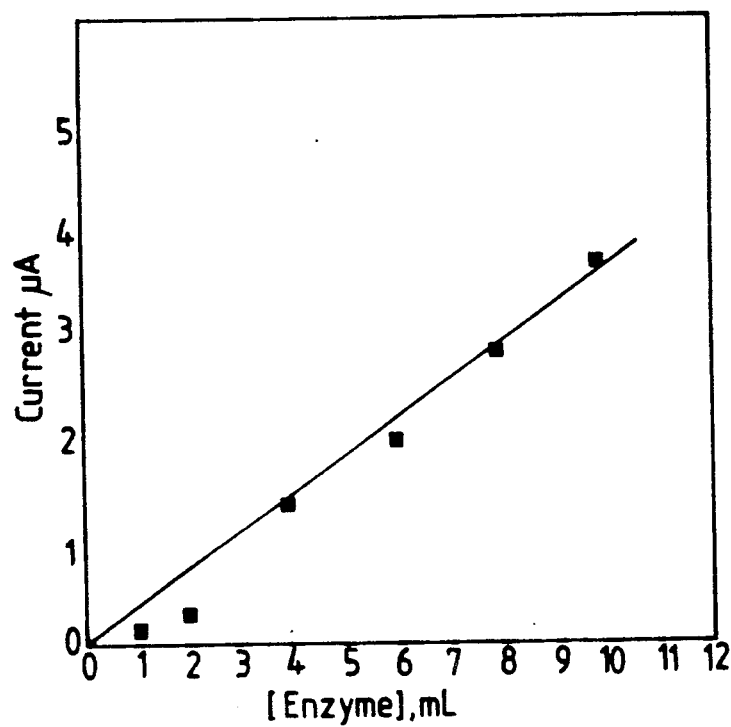
FIG. 6a and 6b show graphs of measurements taken on an pyrrolidonyl aminopeptidase system of Example 7.
Figure 6B:
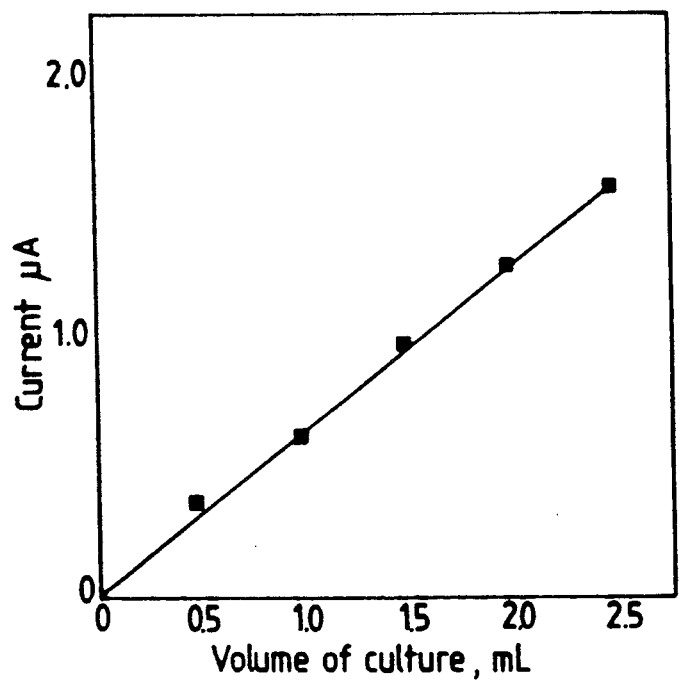

Enzyme activity was assayed using both mammalian pyrrolidonyl aminopeptidase and the enzyme naturally present in Pseudomonas fluorescens ATCC 25289. A calibration curve for the assay of the mammalian enzyme is presented in FIG. 6(a), using 50 mM Tris.HCl, pH 8.3, 25° C., 100 mM NaCl, 1 mM substrate. A calibration curve for Ps. fluorescens is presented in FIG. 6(b), using substrate at 2 mM in buffer as before. A good linear response with bacterial cell numbers was observed. In the case of Ps. fluorescens, the enzyme activity was found to be localised within the cells rather than secreted into the medium.

Further Examples

Although the invention has been illustrated with reference to disposable elements which have a filter, the invention also embraces disposable elements comprising a reference electrode, working electrode, and fusible link. Such electrodes may be manufactured for example by screen printing a substrate as if to make an disposable element in accordance with EP 127958 but further including a fusible link.

We claim:

1. A disposable element for use in analytical equipment for a bioelectrochemical determination, the disposable element comprising a base plate having an aperture for flow of liquid through said element, a working electrode coated on a face of said base plate, a reference electrode coated on said face of said base plate, and a filter in contact with said electrodes for retention of solids in the vicinity of said electrodes for determination.

2. A disposable element according to claim 1, which is a single-use disposable element.

3. A disposable element according to claim 2, which has a fusible electrically conducting link which may be fused to ensure single use of the disposable element.

4. A disposable element according to claim 1, wherein the filter is a depth filter.

5. A disposable element according to claim 1, wherein the disposable element further comprises a counter electrode.

6. A disposable element according to claim 1, wherein at least one of the electrodes is printed.

7. A disposable element according to claim 6, wherein the working electrode and the reference electrode are printed on the same surface.

8. Analytical equipment for a bioelectrochemical determination using a working electrode coated on a face of a base plate having an aperture to allow flow of liquid past said electrode and a reference electrode coated on said face of said base plate, wherein said base plate, working electrode, said reference electrode, and a filter in contact with said electrodes for retention of solids in the vicinity of the electrodes, are provided as a disposable element, and wherein the analytical equipment has receiving means for releasably receiving the disposable element.

9. Analytical equipment for a bioelectrochemical determination using a working electrode coated on a face of a base plate having an aperture to allow flow of liquid past said electrode and a reference electrode coated on said face of said base plate, wherein said base plate, working electrode, said reference electrode and a filter in contact with said base plate for retention of solids in the vicinity of the electrodes, are provided as a disposable element, and wherein the analytical equipment has receiving means for releasably receiving the disposable element, wherein the disposable element is as defined in any of claims 2 or 3.

10. Analytical equipment according to claim 8, wherein there is only one way in which the disposable element can be received in the receiving means.

11. Analytical equipment according to claim 8, wherein the analytical equipment includes an air bubble detector.

12. Analytical equipment according to any of claim 8, wherein the analytical equipment has a supply of enzyme-labelled antibody which antibody immunoreacts with a microorganism to be determined, and a supply of a substrate for the enzyme of the enzyme-labelled antibody which substrate is catalytically converted by the enzyme to a product of electroactivity different to that of the substrate.

13. A disposable element for use in analytical equipment for a bioelectrochemical determination, the disposable element comprising a base plate having an aperture for flow of liquid through said element, a working electrode coated on a face of said base plate, a reference electrode coated on said face of said base plate, a fusible electrically conducting link which may be fused to ensure single use of the disposable element, and a filter in contact with said base plate for retention of solids in the vicinity of said electrodes for determination.

* * * * *

UNITED STATES PATENT AND TRADEMARK OFFICE
CERTIFICATE OF CORRECTION

PATENT NO. : 5,126,034
DATED : June 30, 1992
INVENTOR(S) : Nigel F. Carter, et al It is certified that error appears in the above-indentified patent and that said Letters Patent is hereby corrected as shown below:

Col. 4, line 3; "wiser" should be --wider--.

Signed and Sealed this

Fifth Day of October, 1993

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,126,034

DATED : June 30, 1992

INVENTOR(S) : Nigel F. Carter et al

It is certified that error appears in the above-identified patent and that said Letters Patent is hereby corrected as shown below:

On the title page Insert item:

(30) Foreign Application Priority Data, July 21, 1988 Great Britian 8817421.

Signed and Sealed this

Thirtieth Day of November, 1993

*Attest:*

BRUCE LEHMAN

*Attesting Officer*     Commissioner of Patents and Trademarks